United States Patent
Chandrasekaran et al.

(10) Patent No.: US 10,403,392 B1
(45) Date of Patent: Sep. 3, 2019

(54) DATA DE-IDENTIFICATION METHODOLOGIES

(71) Applicant: ALLSCRIPTS SOFTWARE, LLC, Raleigh, NC (US)

(72) Inventors: Sayee Balaji Chandrasekaran, Raleigh, NC (US); Jeremy Maxwell, Raleigh, NC (US)

(73) Assignee: Allscripts Software, LLC, Raleigh, NC (US)

( * ) Notice: Subject to any disclaimer, the term of this patent is extended or adjusted under 35 U.S.C. 154(b) by 57 days.

(21) Appl. No.: 14/102,522

(22) Filed: Dec. 11, 2013

(51) Int. Cl.
*G16H 10/60* (2018.01)
*G06Q 50/24* (2012.01)

(52) U.S. Cl.
CPC ............. *G16H 10/60* (2018.01); *G06Q 50/24* (2013.01)

(58) Field of Classification Search
CPC .. G06Q 50/22–24; G06Q 50/24; G16H 10/60; G16H 10/00; G16H 10/20; G16H 10/40; G16H 10/65; G16H 15/00; G16H 20/00; G16H 20/10; G16H 20/13; G16H 20/17; G16H 20/30; G16H 20/40; G16H 20/60; G16H 20/70; G16H 20/90; G16H 30/00; G16H 40/00; G16H 40/20; G16H 40/40; G16H 40/60; G16H 40/63; G16H 40/67; G16H 50/00; G16H 70/00; G16H 70/20; G16H 70/40; G16H 70/60; G16H 80/00
See application file for complete search history.

(56) References Cited

U.S. PATENT DOCUMENTS

| | | | |
|---|---|---|---|
| 2005/0165623 A1* | 7/2005 | Landi | G06Q 50/22 705/2 |
| 2006/0074983 A1* | 4/2006 | Jones | G16H 10/65 |
| 2006/0129345 A1* | 6/2006 | Parvin | G01N 35/00594 702/119 |
| 2006/0179075 A1* | 8/2006 | Fay | G06F 21/6245 |
| 2010/0306854 A1* | 12/2010 | Neergaard | G06F 21/6254 726/26 |
| 2011/0123118 A1* | 5/2011 | Nayar | G06T 11/60 382/190 |
| 2012/0041791 A1* | 2/2012 | Gervais | G06F 21/6254 705/4 |
| 2012/0266254 A1* | 10/2012 | Gupta | G06F 21/6254 726/26 |
| 2013/0080398 A1* | 3/2013 | Booth | G06F 21/6254 707/687 |
| 2014/0280261 A1* | 9/2014 | Butler | G06F 21/6254 707/756 |

* cited by examiner

*Primary Examiner* — Linh Giang Le
(74) *Attorney, Agent, or Firm* — Medley, Behrens & Lewis, LLC (57) ABSTRACT

A method includes de-identifying a data table containing protected health information by determining, based on a mappings file, that a first column of the data table is associated with a first data type, accessing each value of the first column, and, for each respective accessed value, automatically generating a de-identified value by applying one or more computer logic instructions associated with de-identification of the first data type to the respective accessed value to result in a respective de-identified value, and saving the respective de-identified value back to the data table in place of the respective accessed value; and utilizing the de-identified data table to test a computer software application.

20 Claims, 4 Drawing Sheets

```xml
<?xml version="1.0" encoding="utf-8" ?>

<mappings-file>
 <database>
    <name>X.X.X.X</name>
    <username>sampleusername</username>
    <password>samplepassword</password>

<!-- The connection string can also be defined the following way -->

<connectionString> DataSource=XYZ; UserID=XYZ; Password=XYZ </connectionString>

<table>
<name>TABLE_NAME</name>
<pk>PRIMARY_KEY</pk>

<mapping datatype="http://www.allscripts.com/deid/datatypes/firstname" column="d_FirstName" gendercolumn column="d_sex" female="F" male="M" />
<mapping datatype="http://www.allscripts.com/deid/datatypes/lastname" column="d_LastName" />
<mapping datatype="http://www.allscripts.com/deid/datatypes/initial" column="d_mi" />
<mapping datatype="http://www.allscripts.com/deid/datatypes/ssn" column="d_SSN" />

<!-- Specifying the SSN config is not mandatory, but you can specify the <value> to be either 'dash format' (XXX-XX-XXXX) or 'space format' (XXX XX XXXX).  Default config, if not specified, is 'no format' (XXXXXXXXX) -->

<configuration>
        <name>DefaultSsnConfiguration</name>
        <key>SsnFormat</key>
        <value>XXX-XX-XXXX</value>
    </configuration>

<mapping datatype="http://www.allscripts.com/deid/datatypes/dateofbirth" column="d_DoB" />
<mapping datatype="http://www.allscripts.com/deid/datatypes/date" column="d_DoD" />
</table>

</database>
</mappings-file>
```

DATA DE-IDENTIFICATION METHODOLOGIES

COPYRIGHT STATEMENT

All of the material in this patent document is subject to copyright protection under the copyright laws of the United States and other countries. The copyright owner has no objection to the facsimile reproduction by anyone of the patent document or the patent disclosure, as it appears in official governmental records but, otherwise, all other copyright rights whatsoever are reserved.

BACKGROUND OF THE INVENTION

The present invention generally relates to data de-identification.

De-identification of personal information is a challenge in any domain in which the use of individual identifiable information has privacy implications. De-identification of such data can be desirable, but can be complex task. Various existing scripts which claim to perform "de-identification" merely scramble data, e.g. by changing "John Smith" and "Jane Doe" to "John Doe" and "Jane Smith". Likewise, in some existing scripts, other fields may be jumbled or including data that isn't semantically accurate. In the healthcare context, such a script not only does not meet HIPAA requirements, but is not 'useful' data for support and testing purposes, as the de-identified data doesn't resemble actual data.

One or more needs exist for improvement in data de-identification. These, and other needs, are addressed by one or more aspects of the present invention.

SUMMARY OF THE INVENTION

The present invention includes many aspects and features. Moreover, while many aspects and features relate to, and are described in, the context of medical data, the present invention is not limited to use only in this context, as will become apparent from the following summaries and detailed descriptions of aspects, features, and one or more embodiments of the present invention.

Accordingly, one aspect of the present invention relates to a method comprising de-identifying a data table containing protected health information by receiving, from a user via an input device associated with an electronic device, input corresponding to mapping, in a mappings file, of each of a plurality of columns of a data table to a respective data type, determining, based on the mappings file, that a first column of the data table is associated with a first data type, accessing each value of the first column, and, for each respective accessed value, automatically generating a de-identified value, based on the identification of the first data type as being associated with the first column in the mappings file, one or more computer logic instructions associated with de-identification of data of the first data type, and the respective accessed value, by applying the one or more computer logic instructions associated with de-identification of the first data type to the respective accessed value to result in a respective de-identified value, and saving the respective de-identified value back to the data table in place of the respective accessed value, determining, based on the mappings file, that a second column of the data table is associated with a second data type, accessing each value of the second column, and, for each respective accessed value, automatically generating a de-identified value, based on the identification of the second data type as being associated with the second column in the mappings file, one or more computer logic instructions associated with de-identification of data of the second data type, and the respective accessed value, by applying the one or more computer logic instructions associated with de-identification of the second data type to the respective accessed value to result in a respective de-identified value, and saving the respective de-identified value back to the data table in place of the respective accessed value, determining, based on the mappings file, that a third column of the data table is associated with the first data type, accessing each value of the first column, and, for each respective accessed value, automatically generating a de-identified value, based on the identification of the first data type as being associated with the first column in the mappings file, one or more computer logic instructions associated with de-identification of data of the first data type, and the respective accessed value, by applying the one or more computer logic instructions associated with de-identification of the first data type to the respective accessed value to result in a respective de-identified value, and saving the respective de-identified value back to the data table in place of the respective accessed value; and providing, by the first user, the de-identified data table to one or more persons or entities for use.

In a feature of this aspect, the first column contains first name data.

In a feature of this aspect, the first column contains last name data.

In a feature of this aspect, the first column contains middle initial data.

In a feature of this aspect, the first column contains birthdate data.

In a feature of this aspect, the first column contains date of death data.

In a feature of this aspect, the first column contains social security number data.

In a feature of this aspect, the first column contains driver's license number data.

In a feature of this aspect, the first column contains patient ID data.

In a feature of this aspect, the first column contains employer data.

In a feature of this aspect, the first column contains URL data.

In a feature of this aspect, the first column contains email address data.

In a feature of this aspect, the first column contains address data.

In a feature of this aspect, the first column contains phone number data.

In a feature of this aspect, the first column contains health plan beneficiary data.

In a feature of this aspect, the first column contains account number data.

In a feature of this aspect, the first column contains vehicle identification number data.

In a feature of this aspect, the first column contains license plate data.

Another aspect relates to a method comprising de-identifying a data table containing protected health information by receiving, from a user via an input device associated with an electronic device, input corresponding to mapping, in a mappings file, of each of a plurality of columns of a data table to a respective data type, determining, based on the mappings file, that a first column of the data table is associated with a first data type, accessing each value of the first column, and, for each respective accessed value, automatically generating a de-identified value, based on the identification of the first data type as being associated with the first column in the mappings file, one or more computer logic instructions associated with de-identification of data of the first data type, and the respective accessed value, by applying the one or more computer logic instructions associated with de-identification of the first data type to the respective accessed value to result in a respective de-identified value, and saving the respective de-identified value back to the data table in place of the respective accessed value, determining, based on the mappings file, that a second column of the data table is associated with a second data type, accessing each value of the second column, and, for each respective accessed value, automatically generating a de-identified value, based on the identification of the second data type as being associated with the second column in the mappings file, one or more computer logic instructions associated with de-identification of data of the second data type, and the respective accessed value, by applying the one or more computer logic instructions associated with de-identification of the second data type to the respective accessed value to result in a respective de-identified value, and saving the respective de-identified value back to the data table in place of the respective accessed value, determining, based on the mappings file, that a third column of the data table is associated with the first data type, accessing each value of the first column, and, for each respective accessed value, automatically generating a de-identified value, based on the identification of the first data type as being associated with the first column in the mappings file, one or more computer logic instructions associated with de-identification of data of the first data type, and the respective accessed value, by applying the one or more computer logic instructions associated with de-identification of the first data type to the respective accessed value to result in a respective de-identified value, and saving the respective de-identified value back to the data table in place of the respective accessed value; and utilizing the de-identified data table to test a computer software application.

Another aspect relates to a non-transitory computer readable medium containing computer executable instructions configured to perform a method comprising determining, based on a mappings file, that a first column of a data table is associated with a first data type, accessing each value of the first column, and, for each respective accessed value, automatically generating a de-identified value, based on the identification of the first data type as being associated with the first column in the mappings file, one or more computer logic instructions associated with de-identification of data of the first data type, and the respective accessed value, by applying the one or more computer logic instructions associated with de-identification of the first data type to the respective accessed value to result in a respective de-identified value, and saving the respective de-identified value back to the data table in place of the respective accessed value, determining, based on the mappings file, that a second column of the data table is associated with a second data type, accessing each value of the second column, and, for each respective accessed value, automatically generating a de-identified value, based on the identification of the second data type as being associated with the second column in the mappings file, one or more computer logic instructions associated with de-identification of data of the second data type, and the respective accessed value, by applying the one or more computer logic instructions associated with de-identification of the second data type to the respective accessed value to result in a respective de-identified value, and saving the respective de-identified value back to the data table in place of the respective accessed value, determining, based on the mappings file, that a third column of the data table is associated with the first data type, and accessing each value of the first column, and, for each respective accessed value, automatically generating a de-identified value, based on the identification of the first data type as being associated with the first column in the mappings file, one or more computer logic instructions associated with de-identification of data of the first data type, and the respective accessed value, by applying the one or more computer logic instructions associated with de-identification of the first data type to the respective accessed value to result in a respective de-identified value, and saving the respective de-identified value back to the data table in place of the respective accessed value.

Another aspect relates to a method comprising de-identifying a data table containing protected health information by receiving, from a user via an input device associated with an electronic device, input corresponding to mapping, in a mappings file, of each of a plurality of columns of a data table to a respective data type, determining, based on the mappings file, that a first column of the data table is associated with a first data type, accessing each value of the first column, and, for each respective accessed value, automatically generating a de-identified value, based on the identification of the first data type as being associated with the first column in the mappings file, one or more computer logic instructions associated with de-identification of data of the first data type, and the respective accessed value, by applying the one or more computer logic instructions associated with de-identification of the first data type to the respective accessed value to result in a respective de-identified value, and saving the respective de-identified value back to the data table in place of the respective accessed value; and utilizing the de-identified data table to test a computer software application.

In addition to the aforementioned aspects and features of the present invention, it should be noted that the present invention further encompasses the various possible combinations and subcombinations of such aspects and features. Thus, for example, any aspect may be combined with an aforementioned feature in accordance with the present invention without requiring any other aspect or feature.

BRIEF DESCRIPTION OF THE DRAWINGS

One or more preferred embodiments of the present invention now will be described in detail with reference to the accompanying drawings, wherein the same elements are referred to with the same reference numerals, and wherein:

FIG. 3 illustrates an exemplary mappings file in accordance with one or more preferred implementations.

DETAILED DESCRIPTION

As a preliminary matter, it will readily be understood by one having ordinary skill in the relevant art ("Ordinary Artisan") that the present invention has broad utility and application. As should be understood, any embodiment may incorporate only one or a plurality of the above-disclosed aspects of the invention and may further incorporate only one or a plurality of the above-disclosed features. Furthermore, any embodiment discussed and identified as being "preferred" is considered to be part of a best mode contemplated for carrying out the present invention. Other embodiments also may be discussed for additional illustrative purposes in providing a full and enabling disclosure of the present invention. As should be understood, any embodiment may incorporate only one or a plurality of the above-disclosed aspects of the invention and may further incorporate only one or a plurality of the above-disclosed features. Moreover, many embodiments, such as adaptations, variations, modifications, and equivalent arrangements, will be implicitly disclosed by the embodiments described herein and fall within the scope of the present invention.

Accordingly, while the present invention is described herein in detail in relation to one or more embodiments, it is to be understood that this disclosure is illustrative and exemplary of the present invention, and is made merely for the purposes of providing a full and enabling disclosure of the present invention. The detailed disclosure herein of one or more embodiments is not intended, nor is to be construed, to limit the scope of patent protection afforded the present invention, which scope is to be defined by the claims and the equivalents thereof. It is not intended that the scope of patent protection afforded the present invention be defined by reading into any claim a limitation found herein that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present invention. Accordingly, it is intended that the scope of patent protection afforded the present invention is to be defined by the appended claims rather than the description set forth herein.

Additionally, it is important to note that each term used herein refers to that which the Ordinary Artisan would understand such term to mean based on the contextual use of such term herein. To the extent that the meaning of a term used herein—as understood by the Ordinary Artisan based on the contextual use of such term—differs in any way from any particular dictionary definition of such term, it is intended that the meaning of the term as understood by the Ordinary Artisan should prevail.

Regarding applicability of 35 U.S.C. § 112, ¶6, no claim element is intended to be read in accordance with this statutory provision unless the explicit phrase "means for" or "step for" is actually used in such claim element, whereupon this statutory provision is intended to apply in the interpretation of such claim element.

Furthermore, it is important to note that, as used herein, "a" and "an" each generally denotes "at least one," but does not exclude a plurality unless the contextual use dictates otherwise. Thus, reference to "a picnic basket having an apple" describes "a picnic basket having at least one apple" as well as "a picnic basket having apples." In contrast, reference to "a picnic basket having a single apple" describes "a picnic basket having only one apple."

When used herein to join a list of items, "or" denotes "at least one of the items," but does not exclude a plurality of items of the list. Thus, reference to "a picnic basket having cheese or crackers" describes "a picnic basket having cheese without crackers", "a picnic basket having crackers without cheese", and "a picnic basket having both cheese and crackers." Finally, when used herein to join a list of items, "and" denotes "all of the items of the list." Thus, reference to "a picnic basket having cheese and crackers" describes "a picnic basket having cheese, wherein the picnic basket further has crackers," as well as describes "a picnic basket having crackers, wherein the picnic basket further has cheese."

Referring now to the drawings, one or more preferred embodiments of the present invention are next described. The following description of one or more preferred embodiments is merely exemplary in nature and is in no way intended to limit the invention, its implementations, or uses.

In accordance with one or more preferred implementations, a de-identification utility is configured to de-identify healthcare data and replace it with realistic "fake" data. In one or more preferred implementations, such replacement is in compliance with privacy requirements of the Health Insurance Portability and Accountability Act (HIPAA), which establishes minimum standards for protecting the privacy of all "individually identifiable health information", sometimes referred to as Protected Health Information (PHI), held or transmitted by a covered entity or its business associate, in any form of media, whether electronic, paper or oral.

One of the ways to meet the minimum security and privacy standards around the use of PHI is to de-identify it, so that the data is no longer considered to be identifiable health information. This relieves the need to employ complex and resource intensive security measures for protecting PHI. For example, a data breach which exposes PHI data could result, owing to regulatory requirements and contractual obligations, in severe fines, bad press, and loss of confidence in the market. The use of de-identification alleviates these concerns, as even in the event of a loss of data, no privacy of any individual has been breached.

In one or more preferred implementations, a de-identification tool functions utilizing a data source and a list of fields that need to be de-identified. In one or more preferred implementations, such a list is included in a mappings file. Preferably, the de-identification tool reads data from the data source, generates realistic "fake" data based on the read data in accordance with an appropriate one of eighteen HIPAA data types in the same format as the read data, and writes the generated "fake" data to a data store (which may or may not be the same as the original data source).

Figure 1:
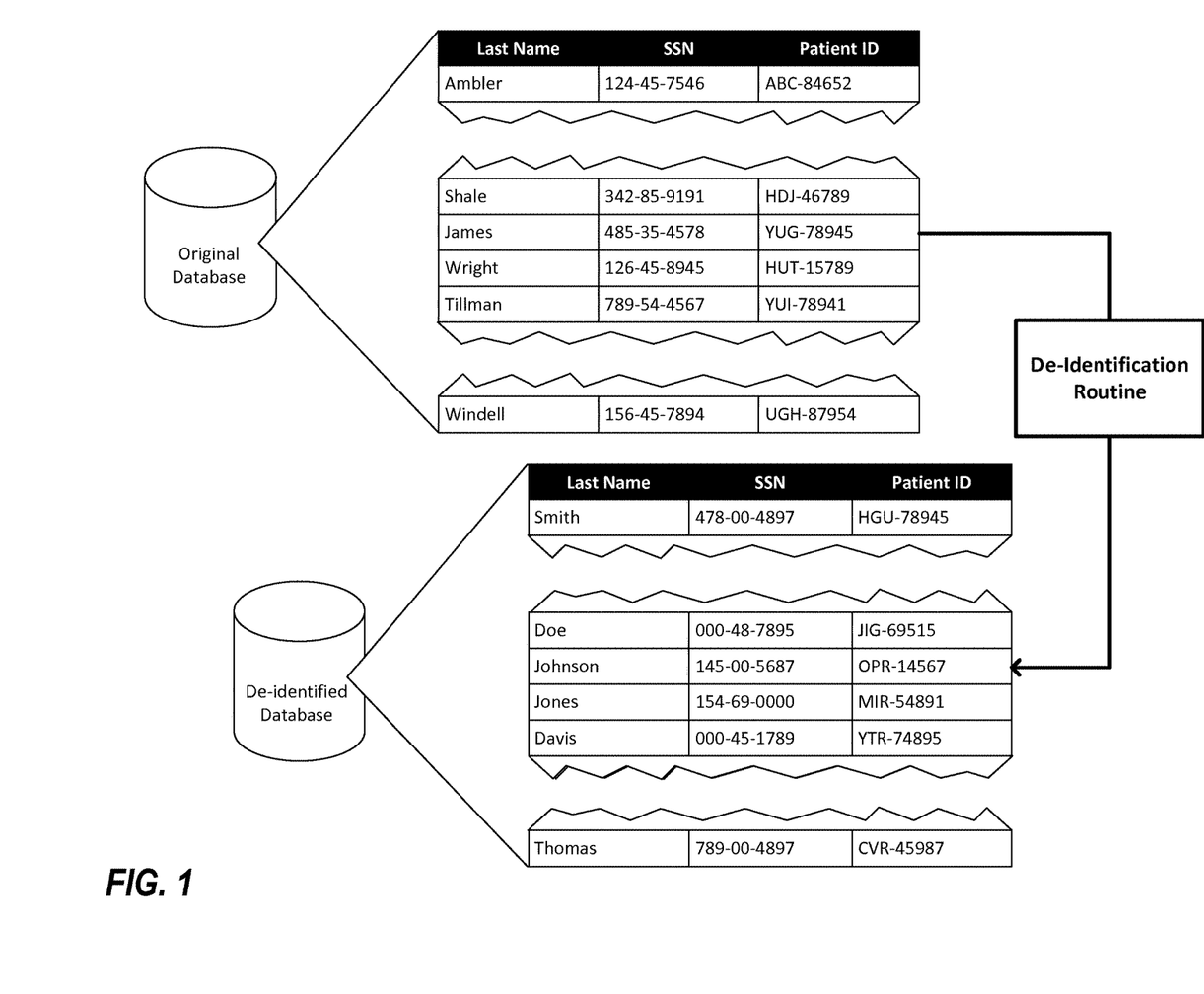
FIG. 1 illustrates the de-identification of original data from a database.

FIG. 1 illustrates the de-identification of original data from a database. In FIG. 1, data from an original database is utilized to generate de-identified data, which is then used to populate a de-identified database. The de-identified data in the de-identified database is free of identifiable information, and can, for example, be used for support and developmental purposes free from the risks associated with storing identifiable health information. It will be appreciated that although FIG. 1 only illustrates three exemplary fields from such a database, these are merely exemplary fields, and the database may (and typically would) have more fields. It will be appreciated that while fields which did include PHI which needed to be de-identified are illustrated, in preferred implementations such a database would frequently additionally include information which would not be de-identified, and would simply be transferred from the original data set to the new de-identified data set. For example, a data set containing patient identifying information and health information for such patients might be de-identified to result in a data set which includes the same health information, but which would simply include "fake" personal information, rather than actual PHI. Such a de-identified data set could subsequently be used for testing and developmental purposes without risking exposure of PHI.

In one or more preferred implementations, a de-identification tool is written in C# using Dependency Injection to allow for multiple configurations based on the objects being de-identified.

Preferably, a Reader object reads original data, one or more Generators create/transform data based on the data types of original data, and a Write object writes the created/transformed data to an output stream. For example, one or more preferred implementations might include a DatabaseReader that reads data from a Database, HipaaGenerators that create fake data according to each of the eighteen HIPAA data types, and a DatabaseWriter that writes generated data (e.g. either back to the database or to a new database). Preferably, each of the HipaaGenerators corresponds to one of the eighteen data types identified by HIPAA.

Preferably, the tool does not read a data source looking for data that is potentially protected health information. Instead, it preferably depends on an input file, which can be characterized as a mappings file, which provides this information. A mappings file maps data types (e.g. the eighteen HIPAA data types) to a data set being de-identified. For example, a mappings file may contain the table and column names for columns to be de-identified, along with the appropriate HIPAA data type for each column.

Section 164.514(b)(2)(i) of the HIPAA Privacy Rule lists the identifiers that must be removed for data to be considered de-identified. Exemplary generators in accordance with one or more preferred implementations which are designed to comply with this HIPAA Privacy Rule will now be described.

In one or more preferred implementations, one or more generators are utilized for the de-identification of name data. In some preferred implementations, these include generators for a male first name, a female first name, and a first name when a gender is unknown. In one or more preferred implementations, the male first name generator randomly selects a name from a list of male names (e.g. a list of the one thousand most common male first names in the U.S.), and the female first name generator similarly randomly selects a name from a list of female names (e.g. a list of the one thousand most common female first names in the U.S.). In one or more preferred implementations, if no gender is specified, a female first name is selected, while in at least some other preferred implementations, a list may be maintained of gender neutral first names.

In one or more preferred implementations, a generator is similarly included for last name generation which randomly selects a last name from a list of last names (e.g. a list of the one thousand most common surnames in the U.S.).

In one or more preferred implementations, a middle name generator may be utilized similar to the first and last name generators, or a middle initiator generator may be utilized which simply randomly generates a middle initial.

In one or more preferred implementations, a street address generator is utilized which selects a random house number from "1" to "9999", and a random street name from a list of street names (e.g. a list of street names which are based on Monopoly property names).

In one or more preferred implementations, a city-state-zip generator is utilized which selects a random city, state, and zip code from a list (e.g. a list containing valid city, state, and zip code tuples for twelve U.S. cities).

In one or more preferred implementations, a birthdate generator is utilized which generates a random month and day. In a preferred implementation, if the birth year in the original data is more than eighty nine years ago, the year will be set to a value corresponding to the current year minus ninety, while if the birth year in the original data is eighty nine years ago or less, then the birth year in the original data will be utilized.

In one or more preferred implementations, a general data generator is utilized for some or all non-birthdate dates. In some preferred implementations, when the tool is first run, a random value between one and fourteen is generated, and all dates are shifted backward in time by that many days, updating month and year where appropriate. Preferably, this days offset value is stored in memory and is not persisted after the tool finishes running.

In one or more preferred implementations, a phone number generator is utilized which generates a random phone number. In some preferred implementations, this phone number is of the form xxx555yyyy.

In one or more preferred implementations, an email address generator is utilized which generates a random email address. For example, this might generate a random "@example.com" email address which comprises ten random characters.

In one or more preferred implementations, a social security number generator is utilized which generates a random social security number (SSN). For example, this might generate a random SSN in the format XXX-YY-ZZZZ where XXX, YY, or ZZZZ are all zeroes, as illustrated in FIG. 1.

In one more preferred implementations, a format preserving generator generates a random value based on original data which respects the format of the original data. For example, if the original data contains six characters, the first three being digits 0-9, and the last three being capital letters A-Z, the format preserving generator will preferably follow these rules while generating fake data. This type of format preserving generator might be used, for example, for medical record numbers, health plan beneficiary numbers, account numbers, certificate/license numbers, vehicle identifiers and serial numbers, license plate numbers, and device identifiers and serial numbers.

In one or more preferred implementations, a driver's license generator generates a random driver's license number. In some preferred implementations, if a state column is specified in a mappings file (e.g. a state field for an address), the generated driver's license number will follow the format for that state. In one or more preferred implementations, if no state is specified in a mappings file, then a default state may be utilized, or a state may be randomly selected.

In one or more preferred implementations, a URL generator generates a random ".com" web address comprising a string of ten random characters selected from A-Z, a-z, and 0-9, followed by ".com". In one or more preferred implementations, rather than only utilizing ".com" addresses, a suffix (e.g. ".com", ".net", or ".biz") may be randomly selected.

In one or more preferred implementations, an image link generator generates a path to a randomly selected one of a default or user configured set of images and image blobs. For example, image data corresponding to a patient photo may be replaced with image data corresponding to a smiley face.

In one or more preferred implementations, an employer generator is utilized which selects a random employer from a list (e.g. a list containing fictitious business entities).

In one or more preferred implementations, a free text generator is utilized which generates text having the same length as original data. In one or more preferred implementations, "Lorem Ipsum" text is generated having the same length as original data.

It will be appreciated that many of the exemplary generators described herein utilize a list (e.g. a list of common first names) which is utilized in generating de-identified data. In one or more preferred implementations, this is a list included at compile time, while in at least some preferred implementations, such a resource list can be specified at run time. In one or more preferred implementations, a default list is utilized unless a different resource list is specified at run time.

As noted hereinabove, in one or more preferred implementations, the tool preferably utilizes a mappings file which maps data types (e.g. the eighteen HIPAA data types) to a data set being de-identified. For example, a mappings file may contain the table and column names in a database that needs to be de-identified, along with the appropriate HIPAA data type for each column.

Figure 2:
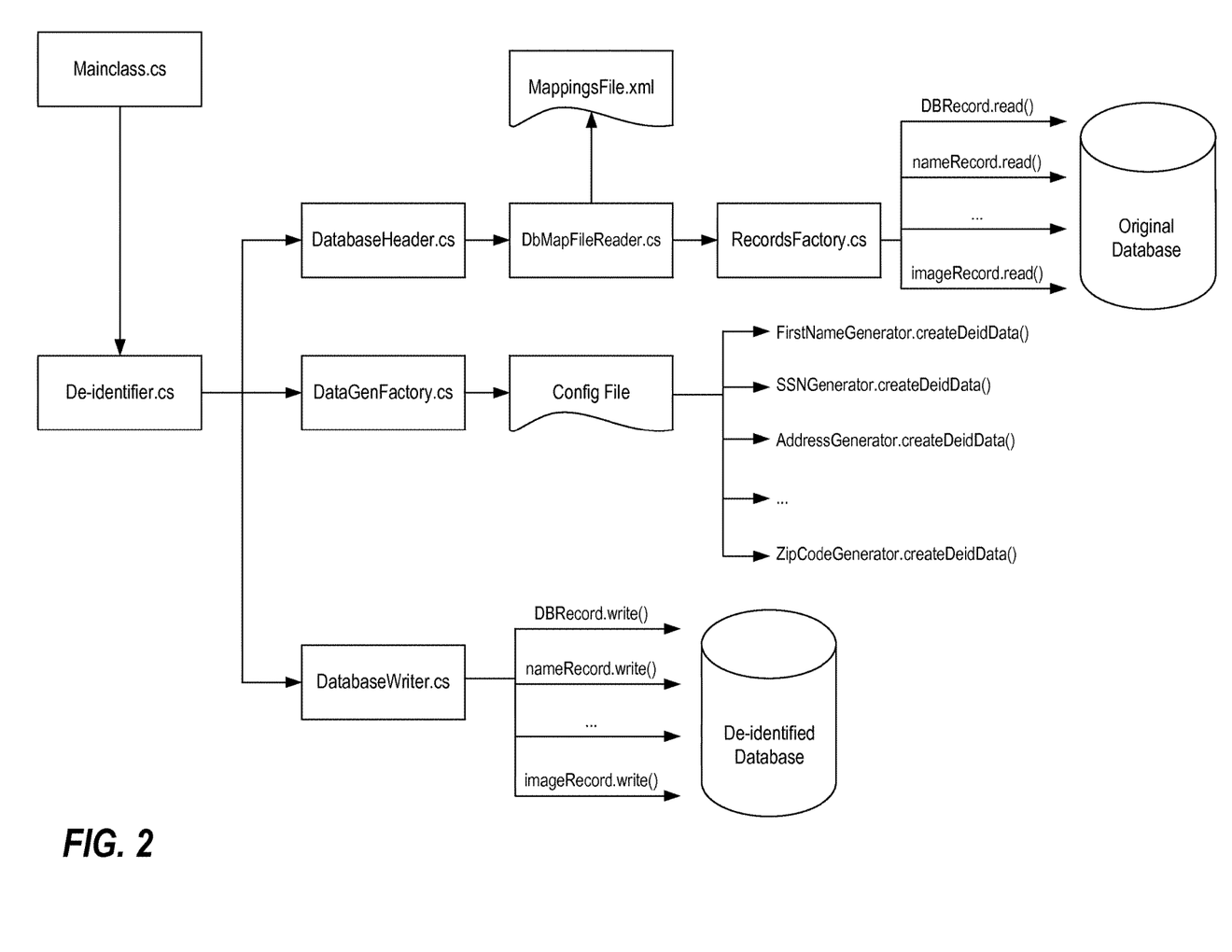
FIG. 2 illustrates an exemplary sequence flow and exemplary interaction of various components of an exemplary tool in accordance with one or more preferred implementations.

FIG. 2 illustrates an exemplary sequence flow and exemplary interaction of various components of an exemplary tool in accordance with one or more preferred implementations, for a scenario where the data source is a database.

As illustrated in FIG. 2, read operations are utilized to read data from a source database informed by a mappings file, and a data generation factory component utilizes this data to generate de-identified data in accordance with a configuration file. This generated de-identified data is then written to a database (which may or may not be the same database) utilizing write operations.

Returning to the example of FIG. 1, a mappings file would be utilized which would specify that values in the "Last Name" column correspond to a "Hipaa Last Name" data type, that values in the "SSN" column correspond to a "Hipaa Social Security Number" data type, and that values in the "Patient ID" column correspond to a "Hipaa Formatted Value" data type. Based on these specifications in the mappings file, data from each column would be read from the original database and de-identified using an appropriate routine selected based on the specified Hipaa data type.

For the values in the "Last Name" column, based on the identification of this column as corresponding to a "Hipaa Last Name" data type, new values would be generated utilizing a last name generator which might, for example, randomly select a last name from a list of the one thousand most common last names in the U.S.

For the values in the "SSN" column, based on the identification of this column as corresponding to a "Hipaa Social Security Number" data type, new values would be generated utilizing a SSN generator which might, for example, generate a random SSN of the format XXX-YY-ZZZZ, where XXX, YY, or ZZZZ are all zeroes.

For the values in the "Patient ID" column, based on the identification of this column as corresponding to a "Hipaa Formatted Value" data type, new values would be generated respecting the format of the original data. In this case, new values would be generated in the format AAA-XXXXX, where AAA is a three character string of alphabetic values A-Z, and XXXXX is a five character string of numeric values 0-9.

Figure 4:
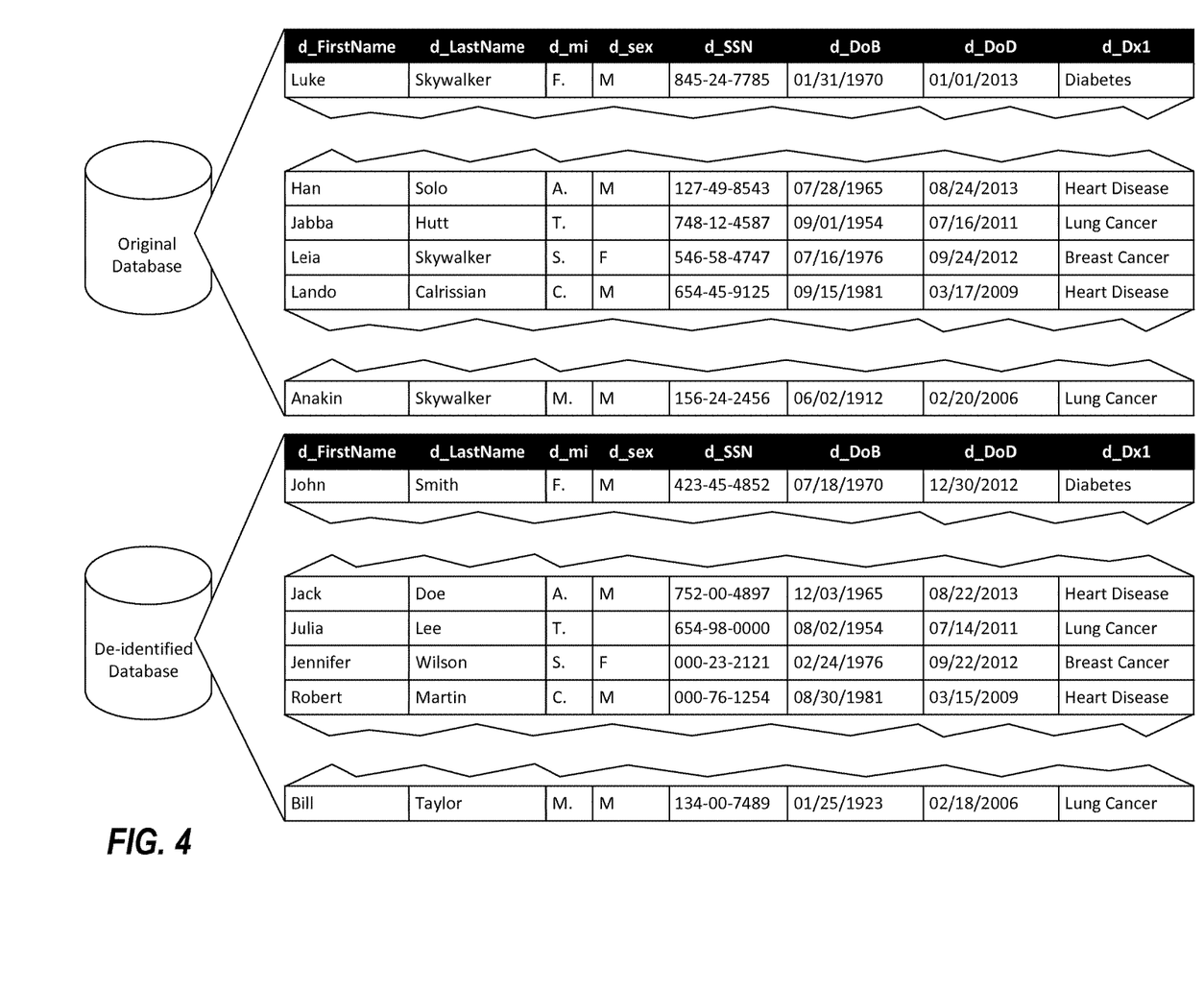
FIG. 4 illustrates the de-identification of a database based on the mappings file of FIG. 3.

FIG. 3 illustrates an exemplary mappings file in accordance with one or more preferred implementations. Specifically, FIG. 3 illustrates a mappings file for the original database illustrated in FIG. 4. The mappings file maps columns of a specified table of the database to data types identified in the mappings file which are stored at specified web addresses. For example, the mappings file maps the d_FirstName column to a firstname data type stored at "http://www.allscripts.com/deid/datatypes/firstname".

Notably, the mappings file can specify an additional column to be utilized by a generator in generating de-identified data. For example, the mappings file, in addition to mapping the d_FirstName column to a firstname data type, further specifies that the d_sex column is to be used to determine a gender, which is "female" if the d_sex column value is "F", and male if the d_sex column value is "male".

Also notable with respect to the example of FIG. 3 is that data that might conventionally be viewed as being of the same data type, for example date of birth and date of death data (both of which might conventionally be viewed as being of a date data type) can be mapped to different data types so as to be given different treatment. In the example of FIG. 3, the d_DoB column is mapped to a dateofbirth data type which generates a random month and date but leaves the year unchanged if it is within the last ninety years, while the d_DoD column is mapped to a date data type which changes the date to be a certain number of days (randomly selected at runtime) prior to the original date.

In one or more preferred implementations, for databases, a tool is configured to take care of scenarios where composite primary keys are defined.

In one or more preferred implementations, a tool has a built-in cache that holds a lookup table for original values and, for each original value, a corresponding value the respective original value was de-identified to. In one or more preferred implementations, before an actual generator call, the lookup table is searched for an entry and, if found, the same value is used. In some preferred implementations, this enhances performance and also maintains integrity in the table, as the same patient will be de-identified to the same value across multiple entries. In one or more preferred implementations, such a cache table is stored as an encrypted file that can be reloaded on a subsequent launch, either automatically or upon user specification.

Although described herein largely in the context of de-identification of a table of a database, one or more preferred implementations are configured to support de-identification of other data sources, such as XML files, HL7 files, claims files, and MOM messages.

In one or more preferred implementations, dependency injection is employed to support multiple configurations based on the objects to be de-identified. One or more preferred implementations utilizing dependency injection are extended to support de-identification of databases, XML files, HL7 files, claims files, MOM messages, and other data sources.

In one or more preferred implementations, a tool is configured for de-identification of XML data. Such a tool may be configured for de-identification of both XML files (e.g. a file stored on a local hard drive), as well as XML data, such as an XML document stored in columns inside of a table.

In one or more preferred implementations for a tool for de-identifying XML data, just as there exists a main mappings file for de-identification of a table as described herein, there is utilized child mappings files for XML files (e.g. a list of data types and tag names). This can comprise, for example, a listing of all tag names and corresponding data types for each tag name. In one or more preferred implementations, a preferred methodology involves building an internal mapping list, parsing column values, determining corresponding data types, and de-identifying to dummy values.

For example, a cell of a data table might include the XML snippet "<SSN>354-52-4513</SSN><patientID>852-AABC</patientID>". In one or more preferred implementations, a child mappings file might map the tag name <SSN> to a certain data type, and the tag name <patientID> to another certain data type.

While tools in accordance with one or more preferred implementations have been described herein in a health care context, in one or more preferred implementations a tool is configured for use in other contexts, such as government, finance, or other industries that handle sensitive information. In one or more preferred implementations, generators, or portions of generators, may be useful in more than one context. For example, in one or more preferred implementations configured for a health care context, an NPI generator, used to generate National Provider Identity numbers, employs the Luhn algorithm, which is the same algorithm commonly used to validate credit card numbers.

Based on the foregoing description, it will be readily understood by those persons skilled in the art that the present invention is susceptible of broad utility and application. Many embodiments and adaptations of the present invention other than those specifically described herein, as well as many variations, modifications, and equivalent arrangements, will be apparent from or reasonably suggested by the present invention and the foregoing descriptions thereof, without departing from the substance or scope of the present invention. Accordingly, while the present invention has been described herein in detail in relation to one or more preferred embodiments, it is to be understood that this disclosure is only illustrative and exemplary of the present invention and is made merely for the purpose of providing a full and enabling disclosure of the invention. The foregoing disclosure is not intended to be construed to limit the present invention or otherwise exclude any such other embodiments, adaptations, variations, modifications or equivalent arrangements, the present invention being limited only by the claims appended hereto and the equivalents thereof.

What is claimed is:

1. A server computing device, comprising:
a processor; and
memory storing instructions that, when executed by the processor, cause the processor to perform steps comprising:
receiving an indication that a software application is to be tested based upon values in a de-identified database; and
responsive to receiving the indication, testing the software application based upon the values in the de-identified database, wherein the de-identified database is constructed based upon a database, wherein the de-identified database has a same format as the database such that fields in the database have corresponding fields in the de-identified database, and further wherein the database comprises:
a row that is representative of a patient; and
a column that is representative of birthdates of patients, wherein the database comprises a field in the row and the column, wherein the field comprises a birthdate of the patient, the birthdate of the patient comprises a first value that identifies a month of birth of the patient, a second value that identifies a day of birth of the patient, and a third value that identifies a year of birth of the patient;
wherein a plurality of acts are undertaken to construct the de-identified database based upon the database, the plurality of acts comprising:
randomly selecting a fourth value to represent a de-identified day of birth;
randomly selecting a fifth value to represent a de-identified month of birth; and
populating a de-identified field in the de-identified database with a de-identified birthdate, the de-identified birthdate comprises the fourth value, the fifth value, and the third value, wherein the de-identified field in the de-identified database corresponds to the field in the database, and further wherein the software application is tested based upon the de-identified birthdate.

2. The server computing device of claim 1, wherein the database further comprises a second column that is representative of surnames of the patients, wherein the database comprises a second field in the row and the second column, wherein the second field comprises a surname of the patient;
wherein the plurality of acts further comprising:
randomly selecting a second surname from a predefined list of surnames; and
populating a second de-identified field in the de-identified database with the randomly selected second surname, wherein the second de-identified field in the de-identified database corresponds to the second field in the database, and further wherein the software application is tested based upon the randomly selected second surname.

3. The server computing device of claim 1, wherein the database further comprises a second column that is representative of given names of the patients, wherein the database comprises a second field in the row and the second column, wherein the second field comprises a given name of the patient;
wherein the plurality of acts further comprising:
randomly selecting a second given name from a predefined list of given names; and
populating a second de-identified field in the de-identified database with the randomly selected second given name, wherein the second de-identified field in the de-identified database corresponds to the second field in the database, and further wherein the software application is tested based upon the randomly selected given name.

4. The server computing device of claim 3, wherein the database further comprises a third column that is representative of genders of the patients, wherein the database comprises a third field in the row and the third column, wherein the third field comprises a gender of the patient;
wherein the plurality of acts further comprising:
selecting the predefined list of given names based upon the gender identified in the third field, wherein the predefined list of given names corresponds to the gender of the patient.

5. The server computing device of claim 1, wherein the database further comprises a second column that is representative of death dates of the patients, wherein the database comprises a second field in the row and the second column, wherein the second field comprises a death date of the patient, the death date of the patient comprises a sixth value that identifies a month of death of the patient, a seventh value that identifies a day of death of the patient, and an eighth value that identifies a year of death of the patient;
  wherein the plurality of acts further comprising:
    randomly selecting a ninth value to represent a de-identified day of death;
    randomly selecting a tenth value to represent a de-identified month of death; and
    populating a second de-identified field in the de-identified database with a de-identified death date, the de-identified death date comprises the ninth value, the tenth value, and the eighth value, wherein the second de-identified field in the de-identified database corresponds to the second field in the database, and further wherein the software application is tested based upon the de-identified death date.

6. The server computing device of claim 1, wherein the database further comprises a second column that is representative of identification numbers of the patients, wherein the database comprises a second field in the row and the second column, wherein the second field comprises an identification number of the patient;
  wherein the plurality of acts further comprising:
    randomly generating a de-identified identification number that has a same format as the identification number of the patient; and
    populating a second de-identified field in the de-identified database with the de-identified identification number, wherein the de-identified second entry in the de-identified database corresponds to the second entry in the database, and further wherein the software application is tested based upon the de-identified identification number.

7. The server computing device of claim 1, wherein the database further comprises a second column that is representative of images of patients, wherein the database comprises a second field in the row and the second column, wherein the second field comprises an image of the patient;
  wherein the plurality of acts further comprising:
    randomly selecting a de-identified image from a predefined list of images; and
    populating a second de-identified field in the de-identified database with the de-identified image, wherein the second de-identified field in the de-identified database corresponds to the second entry in the database, and further wherein the software application is tested based upon the de-identified image of the patient.

8. The server computing device of claim 1, wherein the database further comprises a second column that is representative of social security numbers of patients, wherein the database comprises a second field in the row and the second column, wherein the second field comprises a social security number of the patient;
  wherein the plurality of acts further comprising:
    randomly generating a de-identified social security number, wherein the de-identified social security number has a same format as the social security number; and
    populating a second de-identified field in the de-identified database with the de-identified social security number, wherein the second de-identified field in the de-identified database corresponds to the second field in the database, and further wherein the software application is tested based upon the de-identified social security number.

9. The server computing device of claim 1, wherein the database further comprises a second column that is representative of email addresses of patients, wherein the database comprises a second field in the row and the second column, wherein the second field comprises an email address of the patient;
  wherein the plurality of acts further comprising:
    randomly selecting a second email address from a predefined list of email addresses; and
    populating a second de-identified field in the de-identified database with the second email address, wherein the second de-identified field in the de-identified database corresponds to the second field in the database, and further wherein the software application is tested based upon the second email address.

10. The server computing device of claim 1, wherein the database further comprises a second column that is representative of street addresses of patients, wherein the database comprises a second field in the row and the second column, wherein the second field comprises a street address of the patient, the street address of the patient comprises a sixth value that identifies a house number of the patient, a seventh value that identifies a street name of the patient, an eighth value that identifies a city of the patient, and a ninth value that identifies a state of the patient;
  wherein the plurality of acts further comprising:
    randomly selecting a tenth value to represent a de-identified house number;
    randomly selecting an eleventh value to represent a de-identified street name; and
    populating a second de-identified field in the de-identified database with a de-identified street address, the de-identified street address comprises the tenth value, the eleventh value, the eighth value, and the ninth value, wherein the second de-identified field in the de-identified database corresponds to the second field in the database, and further wherein the software application is tested based upon the de-identified street address.

11. A method executed by a processor of a computing system, the method comprising:
  receiving an indication that a software application is to be tested based upon values in a de-identified database; and
  responsive to receiving the indication, testing the software application based upon the values in the de-identified database, wherein the de-identified database is constructed based upon a database, wherein the de-identified database has a same format as the database such that fields in the database have corresponding fields in the de-identified database, and further wherein the database comprises:
    a row that is representative of a patient; and
    a column that is representative of birthdates of patients, wherein the database comprises a field in the row and the column, wherein the field comprises a birthdate of the patient, the birthdate of the patient comprises a first value that identifies a month of birth of the patient, a second value that identifies a day of birth of the patient, and a third value that identifies a year of birth of the patient;
  wherein a plurality of acts are undertaken to construct the de-identified database based upon the database, the plurality of acts comprising:
    randomly selecting a fourth value to represent a de-identified day of birth;

randomly selecting a fifth value to represent a de-identified month of birth; and populating a de-identified field in the de-identified database with a de-identified birthdate, the de-identified birthdate comprises the fourth value, the fifth value, and the third value, wherein the de-identified field in the de-identified database corresponds to the field in the database, and further wherein the software application is tested based upon the de-identified birthdate.

12. The method of claim 11, wherein the database further comprises a second column that is representative of surnames of the patients, wherein the database comprises a second field in the row and the second column, wherein the second field comprises a surname of the patient;
  wherein the plurality of acts further comprising:
    randomly selecting a second surname from a predefined list of surnames; and
    populating a second de-identified field in the de-identified database with the randomly selected second surname, wherein the second de-identified field in the de-identified database corresponds to the second field in the database, and further wherein the software application is tested based upon the randomly selected second surname.

13. The method of claim 11, wherein the database further comprises a second column that is representative of given names of the patients, wherein the database comprises a second field in the row and the second column, wherein the second field comprises a given name of the patient;
  wherein the plurality of acts further comprising:
    randomly selecting a second given name from a predefined list of given names; and
    populating a second de-identified field in the de-identified database with the randomly selected second given name, wherein the second de-identified field in the de-identified database corresponds to the second field in the database, and further wherein the software application is tested based upon the randomly selected given name.

14. The method of claim 13, wherein the database further comprises a third column that is representative of genders of the patients, wherein the database comprises a third field in the row and the third column, wherein the third field comprises a gender of the patient;
  wherein the plurality of acts further comprising:
    selecting the predefined list of given names based upon the gender identified in the third field, wherein the predefined list of given names corresponds to the gender of the patient.

15. The method of claim 11, wherein the database further comprises a second column that is representative of death dates of the patients, wherein the database comprises a second field in the row and the second column, wherein the second field comprises a death date of the patient, the death date of the patient comprises a sixth value that identifies a month of death of the patient, a seventh value that identifies a day of death of the patient, and an eighth value that identifies a year of death of the patient;
  wherein the plurality of acts further comprising:
    randomly selecting a ninth value to represent a de-identified day of death;
    randomly selecting a tenth value to represent a de-identified month of death; and
    populating a second de-identified field in the de-identified database with a de-identified death date, the de-identified death date comprises the ninth value, the tenth value, and the eighth value, wherein the second de-identified field in the de-identified database corresponds to the second field in the database, and further wherein the software application is tested based upon the de-identified death date.

16. The method of claim 11, wherein the database further comprises a second column that is representative of identification numbers of the patients, wherein the database comprises a second field in the row and the second column, wherein the second field comprises an identification number of the patient;
  wherein the plurality of acts further comprising:
    randomly generating a de-identified identification number that has a same format as the identification number of the patient; and
    populating a second de-identified field in the de-identified database with the de-identified identification number, wherein the de-identified second entry in the de-identified database corresponds to the second entry in the database, and further wherein the software application is tested based upon the de-identified identification number.

17. The method of claim 11, wherein the database further comprises a second column that is representative of images of patients, wherein the database comprises a second field in the row and the second column, wherein the second field comprises an image of the patient;
  wherein the plurality of acts further comprising:
    randomly selecting a de-identified image from a predefined list of images; and
    populating a second de-identified field in the de-identified database with the de-identified image, wherein the second de-identified field in the de-identified database corresponds to the second entry in the database, and further wherein the software application is tested based upon the de-identified image of the patient.

18. The method of claim 11, wherein the database further comprises a second column that is representative of social security numbers of patients, wherein the database comprises a second field in the row and the second column, wherein the second field comprises a social security number of the patient;
  wherein the plurality of acts further comprising:
    randomly generating a de-identified social security number, wherein the de-identified social security number has a same format as the social security number; and
    populating a second de-identified field in the de-identified database with the de-identified social security number, wherein the second de-identified field in the de-identified database corresponds to the second field in the database, and further wherein the software application is tested based upon the de-identified social security number.

19. The method of claim 11, wherein the database further comprises a second column that is representative of email addresses of patients, wherein the database comprises a second field in the row and the second column, wherein the second field comprises an email address of the patient;
  wherein the plurality of acts further comprising:
    randomly selecting a second email address from a predefined list of email addresses; and
    populating a second de-identified field in the de-identified database with the second email address, wherein the second de-identified field in the de-identified database corresponds to the second field in the database, and further wherein the software application is tested based upon the second email address.

20. A computer-readable memory device comprising instructions that, when executed by a processor, cause the processor to perform acts comprising:
receiving an indication that a software application is to be tested based upon values in a de-identified database; and
responsive to receiving the indication, testing the software application based upon the values in the de-identified database, wherein the de-identified database is constructed based upon a database, wherein the de-identified database has a same format as the database such that fields in the database have corresponding fields in the de-identified database, and further wherein the database comprises:
  a row that is representative of a patient; and
  a column that is representative of birthdates of patients, wherein the database comprises a field in the row and the column, wherein the field comprises a birthdate of the patient, the birthdate of the patient comprises a first value that identifies a month of birth of the patient, a second value that identifies a day of birth of the patient, and a third value that identifies a year of birth of the patient;
wherein a plurality of acts are undertaken to construct the de-identified database based upon the database, the plurality of acts comprising:
  randomly selecting a fourth value to represent a de-identified day of birth;
  randomly selecting a fifth value to represent a de-identified month of birth; and
  populating a de-identified field in the de-identified database with a de-identified birthdate, the de-identified birthdate comprises the fourth value, the fifth value, and the third value, wherein the de-identified field in the de-identified database corresponds to the field in the database, and further wherein the software application is tested based upon the de-identified birthdate.

* * * * *